US010350313B2

(12) United States Patent
Yan (10) Patent No.: US 10,350,313 B2
(45) Date of Patent: Jul. 16, 2019

(54) TARGETING APTAMER FOR ATHEROSCLEROSIS AND PREPARATION METHOD AND APPLICATION THEREOF

(71) Applicant: Pengke Yan, Guangzhou (CN)

(72) Inventor: Pengke Yan, Guangzhou (CN)

(73) Assignee: GUANGZHOU TONGPENG ZHONGXU PHARMACEUTICAL CO., LTD., Guangzhou (CN)

( * ) Notice: Subject to any disclaimer, the term of this patent is extended or adjusted under 35 U.S.C. 154(b) by 337 days.

(21) Appl. No.: 14/763,815

(22) PCT Filed: Oct. 14, 2013

(86) PCT No.: PCT/CN2013/001248
§ 371 (c)(1),
(2) Date: Jul. 27, 2015

(87) PCT Pub. No.: WO2018/198010
PCT Pub. Date: Dec. 18, 2014

(65) Prior Publication Data
US 2015/0359910 A1    Dec. 17, 2015

(30) Foreign Application Priority Data

Jun. 14, 2013 (CN) .......................... 2013 1 0237217

(51) Int. Cl.
| | | |
|---|---|---|
| A61K 51/00 | (2006.01) | |
| A61M 36/14 | (2006.01) | |
| A61K 49/18 | (2006.01) | |
| C12N 15/115 | (2010.01) | |
| A61K 49/08 | (2006.01) | |
| G01R 33/56 | (2006.01) | |

(52) U.S. Cl.
CPC ........ *A61K 49/1848* (2013.01); *A61K 49/085* (2013.01); *A61K 49/1851* (2013.01); *A61K 49/1857* (2013.01); *C12N 15/115* (2013.01); *C12N 2310/16* (2013.01); *G01R 33/5601* (2013.01)

(58) Field of Classification Search
CPC ............ A61K 2123/00; A61K 2121/00; A61K 49/00; A61K 49/1848; A61K 49/1851; A61K 49/085; A61K 49/1857; C12N 15/115; C12N 2310/16; G01R 33/5601
USPC ...... 424/1.11, 1.49, 1.69, 1.73, 9.1, 9.2, 9.3, 424/9.32

See application file for complete search history.

(56) References Cited

U.S. PATENT DOCUMENTS

| | | | | |
|---|---|---|---|---|
| 7,727,969 B2* | 6/2010 | Farokhzad | ......... | A61K 48/0041 424/486 |
| 2011/0021970 A1* | 1/2011 | Vo-Dinh | ............ | A61K 49/0039 604/20 |
| 2011/0110867 A1* | 5/2011 | Chung | ............... | A61K 49/0002 424/9.37 |

* cited by examiner

*Primary Examiner* — D. L. Jones
(74) *Attorney, Agent, or Firm* — Gokalp Bayramoglu (57) ABSTRACT

Disclosed are a targeting aptamer for atherosclerosis and a preparation method and application thereof. The targeting aptamer is a targeting aptamer fragment for atherosclerosis obtained through screening of macrophage-derived foam cells together with reverse screening of smooth muscle cells, endothelial cells, and THP-1 cells using a SELEX method; and the use of the targeting aptamer in preparation of an MRI targeting nano-contrast agent for atherosclerosis allows the specific binding of the MRI targeting nano-contrast agent for atherosclerosis only with the macrophage-derived foam cells, and allows high specific binding thereof with vascular tissues with AS lesion, this improving targeting effect of the MRI targeting nano-contrast agent for atherosclerosis and realizing early specific diagnosis of arterial sclerosis.

11 Claims, 10 Drawing Sheets
Specification includes a Sequence Listing.

SEQUENCE LISTING

```
<160> NUMBER OF SEQ ID NOS: 4

<210> SEQ ID NO 1
<211> LENGTH: 45
<212> TYPE: DNA
<213> ORGANISM: Artificial Sequence
<220> FEATURE:
<223> OTHER INFORMATION: In order to improve the specificity of the
      targeting aptamer for atherosclerosis, a nucleotide sequence of
      said targeting aptamer fragment for atherosclerosis is SEQ ID
      No:1. Both ends are fixed sequences, 35 nucleotides in the middle
      is random.
<220> FEATURE:
<221> NAME/KEY: only specifically binds macrophage-derived foam cells,
      binds avascular tissues with AS lesion with a high specificity,
      thus improving the targeting effect of the MRI targeting nano-
      contrast agent for atherosclerosis
<222> LOCATION: (1)..(45)

<400> SEQUENCE: 1
cccctgcagg tgattttgct caagtgtatc gctaatcagg cggat              45

<210> SEQ ID NO 2
<211> LENGTH: 81
<212> TYPE: DNA
<213> ORGANISM: Artificial Sequence
<220> FEATURE:
<223> OTHER INFORMATION: In order to further improve the specificity of
      the targeting aptamer for atherosclerosis, as a preferred
      solution, the nucleotide sequence of said targeting aptamer
      fragment for atherosclerosis is SEQ ID No:2.
<220> FEATURE:
<221> NAME/KEY: only specifically binds macrophage-derived foam cells,
      binds avascular tissues with AS lesion with a high specificity,
      thus improving the targeting effect of the MRI targeting nano-
      contrast agent for atherosclerosis
<222> LOCATION: (1)..(81)

<400> SEQUENCE: 2
cccctgcagg tgattttgct caagttgacc tgaacctacc tcgtttggca cccctcggc   60 agtatcgcta atcaggcgga t                                           81

<210> SEQ ID NO 3
<211> LENGTH: 25
<212> TYPE: DNA
<213> ORGANISM: Artificial Sequence
<220> FEATURE:
<223> OTHER INFORMATION: designing an upstream primer SEQ ID No:3
<220> FEATURE:
<221> NAME/KEY: only specifically binds macrophage-derived foam cells,
      binds avascular tissues with AS lesion with a high specificity,
      thus improving the targeting effect of the MRI targeting nano-
      contrast agent for atherosclerosis
<222> LOCATION: (1)..(25)

<400> SEQUENCE: 3
cccctgcagg tgattttgct caagt                                       25
```

```
<210> SEQ ID NO 4
<211> LENGTH: 21
<212> TYPE: DNA
<213> ORGANISM: Artificial Sequence
<220> FEATURE:
<223> OTHER INFORMATION: a downstream primer SEQ ID No:4
<220> FEATURE:
<221> NAME/KEY: only specifically binds macrophage-derived foam cells,
      binds avascular tissues with AS lesion with a high specificity,
      thus improving the targeting effect of the MRI targeting nano-
      contrast agent for atherosclerosis
<222> LOCATION: (1)..(21)

<400> SEQUENCE: 4
atccgcctga ttagcgatac t                                              21
```

TARGETING APTAMER FOR ATHEROSCLEROSIS AND PREPARATION METHOD AND APPLICATION THEREOF

CROSS REFERENCE TO RELATED APPLICATIONS

This application is the national phase entry of International Application No. PCT/CN2013/001248, filed on Oct. 14, 2013, which is based upon and claims priority to Chinese Patent Application No. 201310237217.X, filed on Jun. 14, 2013, the entire contents of which are incorporated herein by reference.

TECHNICAL FIELD

The invention relates to a reagent for a magnetic resonance diagnosis, in particular to a targeting aptamer for atherosclerosis and preparation method and application thereof.

BACKGROUND

According to the report of World Health Organization (WHO), the number of people died from atherosclerosis (AS) accounts for 52% of the number of people died from all diseases, which is far more than the number of people died from tumours that is the second cause of death (24%) and atherosclerosis has become the first killer threatening human's health. AS mainly involves large and medium scale muscle tension type arteries, wherein thickening of the arterial wall and luminal stenosis are main basis of clinical imaging diagnosis. However, recent studies indicate that the occurrence of clinical events caused by AS, such as acute coronary syndrome, always has no significant relevance with the arterial stenosis caused by AS. The appearance and development of AS is a chronic and progressive process, typical AS conditions can be seen in young adults, but it is not easily to be detected, and serious clinical manifestations always appears a dozen years or several decades latter. Early diagnosis and intervention are crucially important to the disease development and prognosis of AS patients.

Current AS imaging diagnostic technologies are classified into two categories:

1. invasive diagnostic technologies: now they are considered as "gold standard" for diagnosing AS, and comprise intravascular ultrasound, digital angiography, and angioscopy, all of them are invasive diagnostic technologies, wherein a catheter has to be inserted for forming images, their operations are complex, and they have a certain dangerousness and complications;

2. noninvasive AS diagnostic technologies comprise 1) multi-slice helical CT, which can obtain 256 slices simultaneously in less than 25 ms, and can provide an intact coronary angiography within 15 s. Its limitations are that in order to ensure image quality, the heart rate has to be decreased, and the spatial resolution is not high, limited by the time resolution, partial volume effect affects its density measurement, and at noncalcified plaques, especially at places with non-significant stenosis, plaques and blood vessel walls cannot be distinguished; 2) CT angiography, when being, used for AS diagnosis, the display of lesion areas is interfered by skeletal images, removing skeletal images by post processing consumes a long time and the effect is not good.

Magnetic resonance angiography (MRA) is a noninvasive diagnostic technology used for diagnosis of blood vessel diseases in magnetic resonance imaging (MRI); the technology can display the stenosis degree by blood flow imaging, and avoid the disadvantages such as using a nephrotoxic contrast agent and ionizing radiation and the like in CT blood vessel image technology. MRI black blood technique (an imaging technique for observing blood vessel walls by means of the blood flow darkening) can accurately describe initial data, such as the existences, sizes and morphologies etc. of plaques at a high resolution and repeatability, so as to indicate that using MRI for evaluating blood vessel walls is feasible. MRI is suitable for all blood vessel areas, but now mainly used for peripheral angiography, there still are some challenges in the examination of coronary artery diseases, this is mainly because that the diameter of coronary artery is small, the direction thereof is bend, MRI is easily affected by respiration and heart rate, the scanning time is too long and the spatial resolution is low. During MRI imaging for coronary arteriosclerosis, the current bottleneck problem is how to improve the resolution of magnetic resonance images. Ultra-small superparamagnetic iron oxide (USPIO) is constituted by a single crystal core consisting of $Fe_3O_4$ or $Fe_2O_3$ and an outer layer coating. After entering into an applied magnetic field, USPIO particles are distributed unevenly, which makes a non-uniform local magnetic field, generates a magnetizing effect, thus accelerates $T_2$ relaxation of proton dephasing, decreases signals of the tissue where they locates, but their influence to $T_1$ relaxation is relatively small, thus making them have properties of a relatively good negative contrast agent. The half life of USPIO is long, R1/R2 of USPIO is appropriate, and USPIO is low-osmotic in normal blood vessels, so USPIO can perform a first pass imaging and a high resolution scanning in the balanced phase. USPIO can be recognized and swallowed by macrophagocytes in AS plaques, so they can mark AS plaques. Schmitz et al. found that in a part of tumour patients of lymph node mapping, USPIO is swallowed by macrophagocytes in the body, and it can be detected that the focal signal ratio in the inflammatory areas of AS plaques decreases. In animal models, it is demonstrated that the positive rate of iron microparticle histological examination in plaques significantly rises as the dosage increases, and USPIO mainly deposits on unstable plaques, and can be effectively imaged in MRI. Researchers have used USPIO as the contrast agent in MRA for observing renal artery and coronary artery, as a result, they found that the imaging effect of the contrast agent for distal blood vessels and their branches is significant.

However, since there is no targeting guidance, after injected into the body, USPIO mainly are uptaken by Reticuloendothelial system (RES); USPIO has some targeting effect for AS blood vessels but the requirement of clinical diagnosis is difficult to achieve. Therefore, how to realize the targeting enrichment of USPIO in AS blood vessels, it is an important research direction for improving the accuracy rate in MRI diagnosis of AS.

SUMMARY

In order to overcome the deficiency of prior art, the purpose of the present invention is providing a targeting aptamer for atherosclerosis, Which is used for a MRI targeting nano-contrast agent for atherosclerosis, only specifically binds macrophage-derived foam cells, binds avascular tissues with AS lesion with a high specificity, thus improving the targeting effect of the MRI targeting nano-contrast agent for atherosclerosis.

The second purpose of the present invention is providing a method for preparing the targeting aptamer for atherosclerosis.

The third purpose of the present invention is using the above-motioned targeting aptamer for atherosclerosis in an MRI targeting nano-contrast agent for atherosclerosis.

The fourth purpose of the present invention is providing an MRI targeting nano-contrast agent for atherosclerosis, improving the diagnosis effect for atherosclerosis, and lowering the toxic and side effect for normal tissues.

The fifth purpose of the present invention is providing a method for preparing an MRI targeting nano-contrast agent for atherosclerosis.

In order to solve the above-mentioned problems, the technical solution used by the present invention is as follows:

a targeting aptamer for atherosclerosis, characterized in that: the targeting aptamer for atherosclerosis is a targeting aptamer fragment for atherosclerosis obtained through screening of macrophage-derived foam cells together with reverse screening of smooth muscle cells, endothelial cells, and THP-1 cells using a SELEX method.

In order to improve the specificity of the targeting aptamer for atherosclerosis, as a preferred solution, a nucleotide sequence of said targeting aptamer fragment for atherosclerosis is SEQ ID No:1.

In order to further improve the specificity of the targeting aptamer for atherosclerosis, as a preferred solution, the nucleotide sequence of said targeting aptamer fragment for atherosclerosis is a sequence which has at least 80% homology with SEQ ID No:2.

In order to further improve the specificity of the targeting aptamer for atherosclerosis, as a preferred solution, the nucleotide sequence of said targeting aptamer fragment for atherosclerosis is SEQ ID No:2.

A method for preparing the targeting aptamer for atherosclerosis, comprising the following steps using the SELEX method:

1) establish a macrophage-derived foam cell model;

2) constructing a FITC marked random ssDNA library:

3) screening an oligonucleotide aptamer of macrophage-derived foam cells by SELEX: the oligonucleotide aptamer is obtained using screening of macrophage-derived foam cells together with reverse screening of smooth muscle cells, endothelial cells, and THP-1 cells;

4) cloning and sequencing: the oligonucleotide aptamer screened in step 3) is subject to a PCR amplification, the product of the PCR amplification, after purification, is ligated to a pGEM-T vector, then is introduced into competent cells, white colonies are picked out using a blue-white spot screen plate and put into LB liquid medium containing 2 ml ampicillin for culturing, performing a PCR identification, sequencing, observing same by a fluorescence microscope, and picking out a specific aptamer;

5) identification of specific binding between the aptamer and foam cells: adding DPBS solution of above-mentioned specific aptamer and yeast tRNA into THP-1 cells, smooth muscle cells, and macrophage-derived foam cells respectively, incubating same at 37° C. in an incubator for 30 minutes, washing same after removing supernatant, observing under a fluorescence microscope, and obtaining the targeting aptamer fragment for atherosclerosis.

In the above-mentioned preparation method, in step 1), the method for establishing the macrophage-derived foam cell model is: culturing THP-1 cells in a cell culture plate, incubating same with 100 nmol/L PMA for 60-84 hours, inducing same to differentiate into macrophages, then incubating same in 80mg/L oxLDL for 60-84 hours, inducing same to foam cells.

In the above-mentioned preparation method, the method for constructing a FITC marked random ssDNA library is constructing a random ssDNA library with a length of 81 nt using a biological method, the ssDNA library being as the nucleotide sequence of SEQ ID No:1, both ends of the sequence of SEQ ID No:1 are fixed sequences, 35 nucleotides in the middle is a random sequence designing an upstream primer SEQ ID No:3 and a downstream primer SEQ ID No:4, wherein the upstream primer is marked with FITC and the downstream primer is marked with Biotin, the random ssDNA library is subject to a PCR amplification, the PRC product is dissolved in PBS solution after agarose electrophoresis, gel cutting and recovery, binding same with streptavidin magnesphere via a chain with Biotin, performing degeneration, eluting the chain with FITC marker from the streptavidin magnesphere, neutralizing same with hydrochloric acid, precipitating over night, dissolving the precipitate in DPBS solution after centrifugation and drying, and the FITC marked random ssDNA library is obtained.

In the above-mentioned preparation method, during constructing the FITC marked random ssDNA library, the PCR amplification system is; ssDNA template 0.1 ug, 10×PCR buffer 10 ul, $MgCl_2$ 2 ul, dNTPs 1 ul, the upstream primer represented by SEQ ID No:3 50 pmol, the downstream primer represented by SEQ ID No:4 50 pmol, Taq enzyme 2U, supplementing deionized water to 100 ul; the amplification condition is: pre-degeneration at 94° C. for 3 minutes, degeneration at 94° C. for 40 seconds, annealing at 72° C. for 1 minute, extension at 72° C. for 1 minute, finally, extension at 72° C. for 7 minutes again.

As an embodiment of the present invention, the method for preparing the targeting aptamer for atherosclerosis of the present invention further comprises in the reaction of step 4), adding yeast tRNA as a competitive conjugate, and performing a cycle of reverse screening after each cycle of screening.

The use of the targeting aptamer for atherosclerosis of the present invention in the preparation of a MRI targeting nano-contrast agent for atherosclerosis.

A MRI targeting nano-contrast agent for atherosclerosis, comprising the above-mentioned targeting aptamer for atherosclerosis and vector which connected to the targeting aptamer for atherosclerosis.

In the MRI, targeting nano-contrast agent for atherosclerosis, said vector can be selected from glucan coated $Fe_3O_4$, chitosan coated $Fe_3O_4$ or silane coated $Fe_3O_4$ nanoparticle vectors. In a preferred solution of the present invention, said vector is a silane coated $Fe_3O_4$ nanoparticle vector; said targeting aptamer for atherosclerosis is covalently connected to the silane in said vector via. glutaral as a bridge.

In the above-mentioned solution, the mass ratio of said vector and the targeting aptamer is (5-10):1. In said vector, the ratio of the total mass of the ferriferrous oxide nanoparticles and the mass of the silane is 1:(3-8).

The mean particle size of the ferriferous oxide nanoparticles is 10-15 nanometer and the total particle size of the silane coated ferriferrous oxide nanoparticles is 30-100 nanometer.

The magnetic parameters of the MRI targeting nano-contrast agent for atherosclerosis of the present invention are $T_2$ relaxation rate of $0.2842 \times 10^6$ $mol^{-1} \cdot s^{-1}$, and the mass saturated magnetization intensity of 108 $emu \cdot g^{-1}$ Fe.

In order to realize the preferred solution, the silane used in the present invention is 3-aminopropylethoxysilane.

A method for preparing the MRI targeting nano-contrast agent for atherosclerosis, the method comprises following steps:

1) preparation of a silane coated ferriferous oxide nanoparticle vector: using ferric chloride and ferrous sulfate as raw materials, refluxing same under a nitrogen atmosphere, after the end of the refluxing, separating out ferriferrous oxide by using a magnet, and refluxing the ferriferrous oxide with silane after the end of the reaction, obtaining the silane coated ferriferrous oxide nanoparticle vector by a separation using a magnet;

2) synthesis of a contrast agent: washing the silane coated ferriferous oxide nanoparticle vector obtained from step 1) with water and an alcohol alternately, dissolving the above-mentioned targeting aptamer and silane coated ferriferrous oxide nanoparticle vector in PBS solutions respectively, then adding the PBS solution of the targeting aptamer for atherosclerosis into the PBS solution of the silane coated ferriferrous oxide nanoparticle vector, and adding a glutaral, placing same on a shaking table for vibration; separating products with a magnet, removing the supernatant, and washing same with the PBS solution.

In the above-mentioned preparation method, step 1) is carried out according to following steps:

a) preparation of ferriferrous oxide: mixing ferric trichloride and ferrous sulfate at a molar ratio of (1.5-2.5):1, the temperature is set at 27-35° C. when refluxing, slowly dropwise adding ammonia water during the refluxing to pH>9, after curing for 20-40 minutes, raising the temperature to 60° C., continuously refluxing same for 0.5-1.5 hours, then separating out ferriferous oxide with a magnet, and washing same with deionized water and anhydrous ethanol, each 2-4 times, to obtain ferriferrous oxide;

b) preliminary treatment of silane, adding silane into deionized water and stirring same, and dropwise adding glacial acetic acid, adjusting pH to 4-6;

c) coating: adding anhydrous ethanol to the ferriferrous oxide of step a), then adding the silane solution of step b), condensation and reflux, stirring same for 3-6 hours at 55-65° C., stopping the heating, further stirring same down to room temperature, taking the reaction liquid, separating same with a magnet, removing the supernatant, adding deionized water and anhydrous ethanol for washing in sequence, each repeating 2-4 times.

The pH of the PBS solution used in step 2) is 7.4.

In the step 2), the frequency of said shaking table is 100 r/min, the temperature is 25° C., and the vibration time is 0.5-1.5 hours.

Compared with prior art, the beneficial effects of the present invention are: the targeting aptamer for atherosclerosis of the present invention only specifically binds macrophage-derived foam cells, and does not binds macrophages, normal smooth muscle cells, endothelial cells, fat cells, and liver cells etc; the in vivo binding experiments using apolipoprotein E gene knockout mice and New Zealand rabbit high-fat feeding AS model show that the aptamer can bind to vascular tissues with AS lesion with a high specificity. The MRI targeting nano-contrast agent for atherosclerosis of the present invention can distribute to living atherosclerosis plaques in a large amount, this increases the target/nontarget ratio; furthermore, the magnetic resonance images have the advantages of a longer imaging time window, a high spatial and time resolutions, and a good contrast etc., scanning an animal into which the contrast agent of the present invention is introduced results a magnetic resonance image having a clear anatomic structure, high signal noise ratio and good contrast, not only the sizes and sites of atherosclerosis plaques, the anatomical relationship thereof with the surrounding structure and the change of signal strength can be seen, but also the imaging effect of the present invention in different stages of atherosclerosis disease can be seen. The atherosclerosis site and the plaque sizes can be detected using the MRI targeting nano-contrast agent for atherosclerosis of the present invention, and the disease stages also can be further indicated, therefore the early specific diagnosis of atherosclerosis can be realized.

Hereafter the present invention is further described in detail combined with drawings and particular embodiments.

BRIEF DESCRIPTION OF THE DRAWINGS

FIGS. 5-7 respectively are the 7T MRI photos of AS mouse group 30 min, 45 min and 120 min after being injected the contrast agent of the present invention; in FIG. 5, where the white arrow points is AS lesion area; in FIG. 6, where the white arrow points is multiple spot signal absent of AS lesion area; in FIG. 7, where the white arrow points is signal recover of AS lesion area;

FIGS. 8-10 respectively are the 7T MRI photos of AS mouse group 30 min, 45 min and 120 min after being injected magnetic ferriferrous oxide nanoparticles; in FIG. 8, where the white arrow points is AS lesion area; in FIG. 9, the AS lesion signal does not change at which the white arrow points, in FIG. 10, the AS lesion signal does not change at which the white arrow points;

FIGS. 11-13 respectively are the 7T MRI photos of normal mouse group 30 mm, 45 min and 120 min after being injected the contrast agent of the present invention; in FIG. 11, where the white arrow points is normal artery; in FIG. 12, where the white arrow points is normal artery, no signal changes; in FIG. 13, where the white arrow points is normal artery, no signal changes;

FIGS. 14-16 respectively are the 7T MRI photos of normal mouse group 30 mM, 45 min and 120 min after being injected magnetic ferriferrous oxide nanoparticles; in FIG. 14, where the white arrow points is normal artery; in FIG. 15, where the white arrow points is normal artery, no signal changes; in FIG. 16, where the white arrow points is normal artery, no signal changes;

FIGS. 17-20 respectively are the 3.0T MRI photos of AS New Zealand rabbit group 0 h, 1 h, 2 h, 3 h after being injected the contrast agent of the present invention; in FIG. 17, where the white arrow points is AS lesion area; in FIG. 18, where the white arrow points, the AS lesion area signal gradually disappear, the vascular wall is unclear; in FIG. 19, where the white arrow points is signal spotted absent of AS lesion area; in FIG. 20, where the white arrow points is signal recover of AS lesion area;

FIGS. 21-24 respectively are the 3.0T MRI photos of AS New Zealand rabbit group 0 h, 1 h, 2 h, 3 h after being injected magnetic ferriferrous oxide nanoparticles; in FIG. 21, where the white arrow points is AS lesion area; in FIG. 22, where the white arrow points is AS lesion area, no signal changes; in FIG. 23, where the white arrow points is AS lesion area, no signal changes; in FIG. 24, where the white arrow points is AS lesion area, no signal changes;

FIGS. 25-28 respectively are the 3.0 T MRI photos of normal New Zealand rabbit group 0 h, 1 h, 2 h, 3 h after being injected the contrast agent of the present invention; in FIG. 25, where the white arrow points is normal blood vessel; in FIG. 26, where the white arrow points is normal blood vessel, no signal changes; in FIG. 27, where the white arrow points is normal blood vessel, no signal changes; in FIG. 28, where the white arrow points is normal blood vessel, no signal changes;

FIGS. 29-32 respectively are the 3.0 T MRI photos of normal New Zealand rabbit group 0 h, 1 h, 2 h, 3 h after being injected magnetic ferriferrous oxide nanoparticles; in FIG. 29, where the white arrow points is normal blood vessel; in FIG. 30, where the white arrow points is normal blood vessel, no signal changes; in FIG. 31, where the white arrow points is normal blood vessel, no signal changes; in FIG. 32, where the white arrow points is normal blood vessel, no signal changes.

DETAILED DESCRIPTION OF THE EMBODIMENTS

Example 1

A targeting aptamer for atherosclerosis, the preparation method thereof is:

1) culturing smooth muscle cells: SD rats, either gender, the body weight is 150-200 g, age is 4-8 weeks: after intraperitoneal anesthesia, taking out thoracic aorta segment by sterile operation, placing same in a plate containing PBS solution for rinsing 3 times, after rinsing the clots clean, stripping the fibrofatty layer of the adventitia, then cutting the blood vessel open in longitudinal direction, striking off intima, i.e. endothelial cells, rapidly tearing down the inner layer and middle layer of the medial membrane, cutting same into 1 mm wide small strips, steeping same in PBS solution containing blood serum, and planting the cut small tissue blocks on the culture bottle wall, putting same in an incubator at 37° C. for about 2 h, taking out the culture bottle, adding a culture solution containing 20% fetal calf serum, then putting same back to the incubator for stationary culture for 4 days, after the cells overspread the bottom, performing digestion passage using 0.25% trypsin, once every 2-3 days, culturing the cells in a 6 well plate before the experiments;

2) culturing endothelial cell line: culturing endothelial cell line using high sugar DMEM medium containing 15% new-born calf serum in a $CO_2$ incubator with 5% $CO_2$ and saturated humidity at 37°C. Performing digestion passage using 0.25% trypsin, once every 2-3 days, culturing the cells in a 6 well plate before the experiments;

3) culturing THP-1 cells: culturing THP-1 cell line using RPMI1640 medium containing 10% new-born calf serum in a $CO_2$ incubator with 5% $CO_2$ and saturated humidity at 37° C.; Performing passage using a direct separating bottle method, once every 2-3 days, culturing the cells in a 6 well plate before the experiments;

4) establishing a macrophage-derived foam cell model: culturing above-mentioned THP-1 cells in 6 well plate using RPMI1640 medium containing 10% new-born calf serum in an incubator with 5% $CO_2$ at 37° C., before each experiment, using 100 nmol/L PMA to incubate the cells for 72 hours, inducing same to differentiate into macrophages, then incubating same in 80 mg/L oxLDL for 72 hours, and inducing same into foam cells;

5) constructing an FITC marked random ssDNA library: constructing a random ssDNA library with a length of 81 nt using a biological method, the ssDNA library being as the nucleotide sequence of SEQ ID No:1, both ends of the sequence of SEQ ID No:1 are fixed sequences, 35 nucleotides in the middle is a random sequence; designing an upstream primer SEQ ID No:3 and a downstream primer SEQ ID No:4, wherein the upstream primer is marked with FITC and the downstream primer is marked with Biotin, the random ssDNA library is subject to a PCR amplification, the PCR amplification system is: ssDNA template 0.1 ug, 10×PCR buffer 10 ul, $MgCl_2$ 2 ul, dNTPs 1 ul, the upstream primer represented by SEQ ID No:3 50 pmol, the downstream primer represented by SEQ ID No:4 50 pmol, Taq enzyme 2U, supplementing deionized water to 100 ul; the amplification condition is: pre-degeneration at 94° C. for 3 minutes, degeneration at 94° C. for 40 seconds, annealing at 72° C. for 1 minute, extension at 72° C. for 1 minute, finally, extension at 72° C. for 7 minutes; the PRC product is dissolved in PBS solution after agarose electrophoresis, gel cutting and recovery, binding same with streptavidin magnesphere via a chain with Biotin; washing same with PBS solution 3 times, performing degeneration using 0.15 mol/L NaOH at 37° C. for 15 minutes, eluting the other chain with FITC marker from streptavidin magnesphere neutralizing same with a little hydrochloric acid, adding 2 volumes of anhydrous ethanol, precipitating same in a −80° C. refrigerator for 3 hours of over night, centrifuging same at 12000 rpm for 30 minutes, removing the supernatant, washing same with 70% ethanol once, dissolving same in DPBS solution after drying in the air, determining the ssDNA concentration using an ultraviolet spectrophotometer, and using same in the next cycle of screening;

6) screening an oligonucleotide aptamer of macrophage-derived foam cells by SELEX: adding about 800 pmol random ssDNA library into a microcentrifuge tube, performing degeneration at 80° C. for 10 minutes, then placing same on ice for annealing 10 minutes. Washing with 37° C. washing buffer 6 times before screening of smooth muscle cells, macrophages, and macrophage-derived foam cells. Adding the library and 2 ml 37° C. 1×binding Buffer, in sequence, into the six well plate in which about 1×10$^6$ smooth muscle cells and macrophages are cultured, incubating same for 30 minutes respectively, then transferring the supernatant into a six well plate in which about 1×10$^6$ foam cells are cultured, incubating same for 30 minutes, removing the supernatant, washing same with 37° C. washing butler 6 times, washing off ssDNA which does not bind foam cells, then adding 800 ul eluant, performing heat denaturation at 80° C. for 10 minutes, taking the supernatant and centrifuging same at 800 rpm for 5 minutes, discarding the small amount of precipitate of the lower layer, adding 2 volumes of pre-cooled anhydrous ethanol, precipitating same in a −80° C. refrigerator for 3 hours or overnight, centrifuging same at 12000 rpm for 30 minutes, washing same with 70% ethanol once, drying same in the air, dissolving same in a small amount of TE or sterile water, determining the ssDNA concentration using an ultraviolet spectrophotometer, PCR amplifying same with TFITC and Biotin marked primers to double marked dsDNA for the next cycle of screening; repeating the above-mentioned steps, screening for 18 cycles repeatedly, all the screening process is in a darkroom or under a dark condition; after performing each cycle of screening, performing a reverse screening to remove the ssDNA ingredients binding the six well plate, smooth muscle cells and macrophages; in order to enhance the specificity of the screening, adding yeast tRNA into the reaction as a competitive conjugate; after performing each cycle of screening, performing a reverse screening to remove the ssDNA ingredients binding the six well plate, smooth muscle cells and macrophages;

7) cloning and sequencing: after 18 cycles of SELEX screening, PCR amplifying ssDNA with upstream primer SEQ ID No:3 and upstream primer SEQ ID No:4 using the amplification product for 2% agarose electrophoresis, cutting the target band on a UV transmission reflectometer, cutting same up and putting into a centrifugal column of a high performance DNA purification and recovery kit, the centrifugal column is put into a 1.5 ml EP tube, centrifuging at 12000 rpm for 1 minute, discarding the centrifugal column, adding 1110 volume of 3 mol/L NaAC (pH 5.2) and 2 volumes of pre-cooled anhydrous ethanol into the EP tube, mixing same evenly on a vortex, putting same in a −80° C. refrigerator for 3 hours or overnight, ligating same with pGEM-T vector, then placing same on ice, picking a small amount of bacterium liquid with an inoculating loop and inoculating same on a LB plate without antibiotics, culturing same in an incubator at 37° C. overnight, after monoclonal colonies appear, picking a clone with an inoculating loop and putting same in a tube containing 2 ml LB medium, shaking the tube in a constant temperature vibrator at 37° C. and 150 rpm overnight, taking 0.5 ml bacterium liquid and adding same in a 250 ml conical flask containing 50 ml LB medium, putting the conical flask in a constant temperature vibrator and shaking at 37° C. and 150 rpm until the absorbance value at 600 nm of the bacterium liquid being about 0.35, placing the bacterium liquid on ice for 10 minutes, centrifuge same in a 50 ml centrifuge tube at 4000 rpm for 5 minutes, removing the supernatant and sucking the residual liquid dry, adding 16 ml solution A, gently resuspending the lower layer cells and placing same on ice for 15 minutes, centrifuging same at 4° C. and 4000 rpm for 5 minutes, collecting the cells, adding 4 ml solution A and gently resuspending the cells, subpackaging the cells at 200 ul/tube, storing same at −70° C. and making same into competent cells, placing 200 ul competent cells on ice for thawing, and then adding 2 ul ligation product, gently mixing the mixture evenly, placing same on ice for 20 minutes, heat shocking same in 42° C. water bath for 90 seconds, placing same on ice for 2 minutes. adding 500 ul 37° C. preheated LB medium without antibiotics, vibrating and culturing same at 37° C. and 150 rpm for 1.5 hours, taking 200 ul bacterium liquid, evenly coating same on a prepared blue-white spot screen plate with a spreader, culturing same at 37° C. for 16-18 hours, placing the plate with colonies in a 4° C. refrigerator for 2 hour, making the blue-white spots develop fully, randomly picking 45 white colonies, putting same into LB liquid medium containing 2 ml ampicillin, after shaking same in a constant temperature vibrator at 37° C. and 150 rpm overnight, taking 5 ul bacterium liquid for each clone for performing a PCR identification; observing by means of a fluorescence microscope, picking out a specific monoclone; sequencing the pickied specific aptamer;

8) identification of specific binding between the aptamer and macrophage-derived foam cells: respectively washing $1\times10^6$ THP-1 macrophages and smooth muscle cells, and $1\times10^6$ macrophage-derived foam cells which are cultured in a six well plate with 37° C. PBS three times, then adding 37° C. DPBS solution containing 200 pmol FITC marked aptamer and 1 ug yeast tRNA, incubating same at 37° C. in an incubator for 30 minutes, washing same with 37° C. PBS three times after removing supernatant, observing and shooting same by means of a fluorescence microscope, and the targeting aptamer fragment for atherosclerosis is obtained.

Specific Detection of Targeting Aptamer for Atherosclerosis

1) Manufacture of Atherosclerosis paraffin sections

Bleeding an atherosclerosis model rabbit to death, taking out the aorta from ascending aorta to the arterial branch of arteria iliaca communis, washing out blood with PBS, fixing same with 10% formalin, performing conventional dehydration, imbedding same with paraffin, serial sectioning same with a Leitz1560 section cutter.

2) Observing the binding between the aptamer and atherosclerosis plaques taking an artery section having plaques and a normal artery section, conventional dewaxing same with xylene to water, dropwise adding 3% hydrogen peroxide, keeping same under room temperature for 5-10 minutes to inactivate endogenous enzymes, washing same with distilled water 3 times. Steeping the sections in 0.01 M citrate buffer (pH 6.0), heating same to boiling with an electric oven or microwave oven, after 5-10 minutes, repeating 1-2 times to repair antigens. After cool down, washing with PBS (pH 7.2-7.6) 1-2 times. Dropwise adding 50 pmol FITC marked targeting aptamer for atherosclerosis of the present invention and 1 ug pmol yeast tRNA, incubating same in an incubator at 37° C. for 30 minutes, washing same with deionized water once for 5 minutes, than washing same with PBS 2 times, each time 5 minutes, observing and shooting the binding between the aptamer and atherosclerosis plaques or normal artery by means of a fluorescence microscope.

The results show that all the targeting aptamers for atherosclerosis prepared by the present invention specifically bind macrophage-derived foam cells, but almost never bind THP-1 macrophages, blood vessel smooth muscle cells, and endothelial cells.

Application Example 1

Preparing a MRI targeting nano-contrast agent for atherosclerosis using the targeting aptamer for atherosclerosis of example 1, the particular steps are:

a) preparation of a silane coated ferriferrous oxide nanoparticle vector: mixing ferric trichloride and ferrous sulfate at a molar ratio of 2:1, using nitrogen for protection, the temperature is set at 30° C. when refluxing, slowly dropwise adding ammonia water during the refluxing to pH>9, after curing for 30 minutes, raising the temperature to 60° C., continuously refluxing for 1 hour, then separating out ferriferrous oxide with a magnet, and washing same with deionized water and anhydrous ethanol in sequence, each 3 times, to obtain ferriferrous oxide; adding 3-aminopropylethoxysilane into deionized water, stirring same under room temperature, dropwise adding glacial acetic acid, adjusting pH to pH≈5; placing alcohol washed $Fe_3O_4$ in a flask, adding anhydrous ethanol, then adding 3-aminopropylethoxysilane at pH≈5 (wherein the mass ratio of 3-aminopropylethoxysilane and $Fe_3O_4$ is 5:1), using nitrogen for protection, reflux condensation, stirring same at 60° C. for 5 hours, stop heating, further stirring same to room temperature, taking the reaction liquid, performing separation with a magnet, removing the supernatant, washing same with deionized water and anhydrous ethanol in sequence, each 3 times, and the silane coated ferriferrous oxide nanoparticle vector is obtained;

b) synthesis of a contrast agent: washing the silane coated ferriferrous oxide nanoparticle vector obtained from step a) with water and an alcohol alternately, finally dissolving same in PBS solutions at pH=7.4; then adding the PBS solution at pH=7.4 to dissolve the targeting aptamer for atherosclerosis represented by SEQ ID No:2, and adding the above-mentioned vector solution, and finally adding a glutaral, placing same on a shaking table for vibration at 100 r/min and 25° C.; for 1 hour; separating products with a magnet, removing the supernatant, and washing the products with the PBS solution, repeating 3 times.

Application Example 2

Preparing a MRI targeting nano-contrast agent for atherosclerosis using the targeting aptamer for atherosclerosis represented by SEQ ID No:2, the particular steps are:

1) preparation of a slime coated ferriferrous oxide nanoparticle vector: mixing ferric trichloride and ferrous sulfate at a molar ratio of 1.5:1, using nitrogen for protection, the temperature is set at 27° C. when refluxing, slowly dropwise adding ammonia water during the refluxing to pH>9, after curing for 40 minutes, raising the temperature to 60° C., continuously refluxing for 1.5 hour, then separating out ferriferrous oxide with a magnet, and washing same with deionized water and anhydrous ethanol in sequence, each 2 times, to obtain ferriferrous oxide; adding 3-aminopropylethoxysilane into deionized water, stifling same under room temperature, dropwise adding glacial acetic acid, adjusting pH to pH≈5; placing alcohol washed $Fe_3O_4$ in a flask, adding anhydrous ethanol, then adding 3-aminopropylethoxysilane at pH≈5 (wherein the mass ratio of 3-aminopropylethoxysilane and $Fe_3O_4$ is 3:1), using nitrogen for protection, reflux condensation, stirring same at 60° C. for 3 hours, stop heating, further stirring same to room temperature, taking the reaction liquid, performing separation with a magnet removing the supernatant, washing same with deionized water and anhydrous ethanol in sequence, each 2 times, and the silane coated ferriferrous oxide nanoparticle vector is obtained;

2) synthesis of a contrast agent: washing the slime coated ferriferrous oxide nanoparticle vector obtained from step 1) with water and an alcohol alternately, finally dissolving same in PBS solutions at pH=7.4; then adding the PBS solution at pH=7.4 to dissolve the targeting aptamer for atherosclerosis represented by SEQ ID No.:2, and adding the above-mentioned vector solution, and filially adding a glutaral, placing same on a shaking table for vibration at 100 r/min and 25° C. for 1 hour; separating products with a magnet, removing the supernatant, and washing the products with the PBS solution, repeating 3 times.

Application Example 3

Preparing a MRI targeting nano-contrast agent for atherosclerosis using the targeting aptamer for atherosclerosis represented by SEQ. ID No:2, the particular steps are:

1) preparation of a silane coated ferriferrous oxide nanoparticle vector: mixing ferric trichloride and sulphates of iron at a molar ratio of 2.5:1, using nitrogen for protection, the temperature is set at 35° C. when refluxing, slowly dropwise adding ammonia water during the refluxing to pH>9, after curing for 20 minutes, raising the temperature to 60° C. continuously refluxing for 1.5 hour, then separating out ferriferrous oxide with a magnet, and washing same with deionized water and anhydrous ethanol in sequence, each 4 times, to obtain ferriferrous oxide; adding 3-aminopropylethoxysilane into deionized water, stirring same under room temperature, dropwise adding glacial acetic acid, adjusting pH to pH≈5: placing alcohol washed $Fe_3O_4$ in a flask, adding anhydrous ethanol, then adding 3-aminopropylethoxysilane at pH≈5 (wherein the mass ratio of 3-aminopropylethoxysilane and $Fe_3O_4$ is 8:1), using nitrogen for protection, reflux condensation, stirring same at 65° C. for 6 hours, stop heating, further stirring same to room temperature, taking the reaction liquid performing separation with a magnet, removing the supernatant, washing same with deionized water and anhydrous ethanol in sequence, each 4 times, and the silane coated ferriferrous oxide nanoparticle vector is obtained;

2) synthesis of a contrast agent: washing the silane coated ferriferrous oxide nanoparticle vector obtained from step 1) with water and an alcohol alternately, finally dissolving same in PBS solutions at pH=7.4; then adding the PBS solution at pH=7.4 to dissolve the targeting aptamer for atherosclerosis represented by SEQ. ID No:2, and adding the above-mentioned vector solution, and finally adding a glutaral, placing same on a shaking table for vibration at 100 r/min and 25° C. for 1 hour; separating products with a magnet, removing the supernatant, and washing the products with the PBS solution, repeating 3 times.

Figure 1:
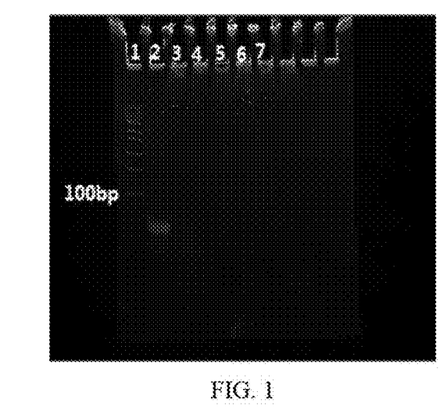
FIG. 1 is the polyacrylamide gel electrophoresis photo of the contrast agent of the present invention: 1: 100 bp Mark; 2: 5'-NH$_2$-targeting aptamer; 3-6: the final product of 0.1, 0.2, 0.5, 1 mL 3-aminoproppyltriethoxysilane coated Fe$_3$O$_4$ coupling with 33 μg 5'-NH$_2$-targeting aptamer; 7: 3-aminopropyltriethoxysilane coated Fe$_3$O$_4$.
Figure 2:
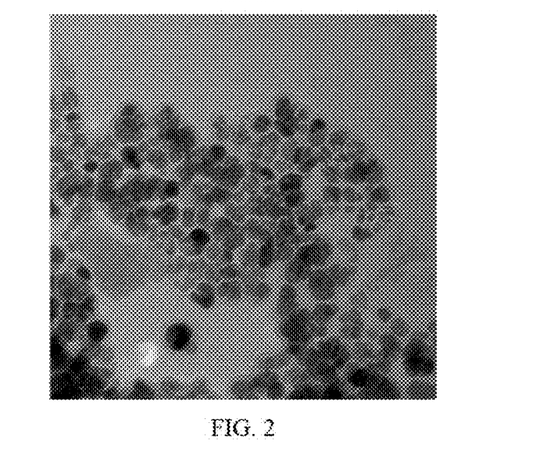
FIG. 2 is the transmission electron microscope photo in the detection method using the contrast agent of the present invention.
Figure 3:
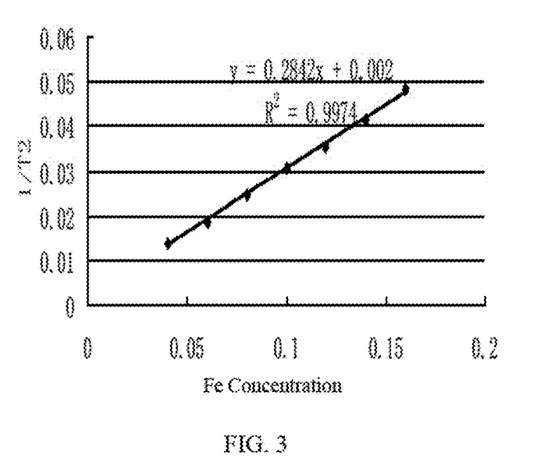
FIG. 3 is the relaxation rate profile of the silane coated ferriferous oxide nanoparticle vector of the present invention.
Figure 4:
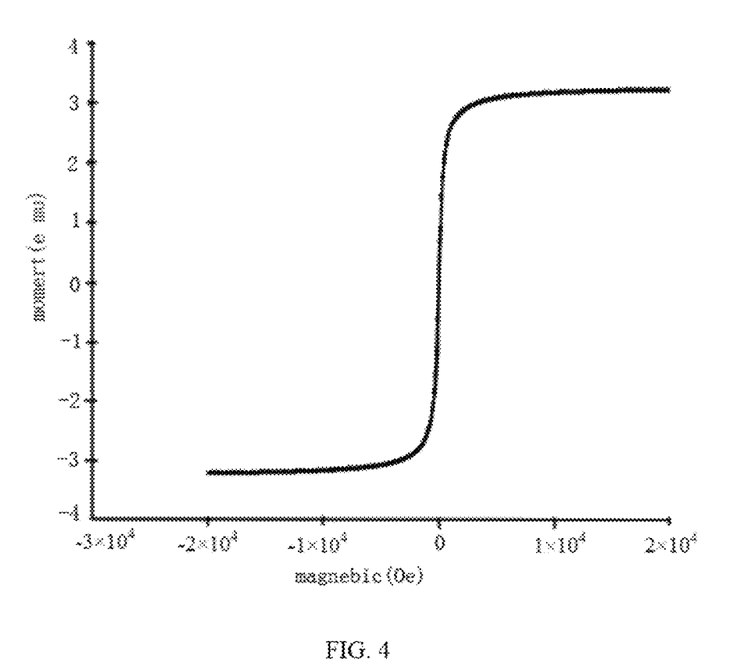
FIG. 4 is the magnetization curve of the silane coated ferriferous oxide nanoparticle vector of the present invention.
Figure 5:
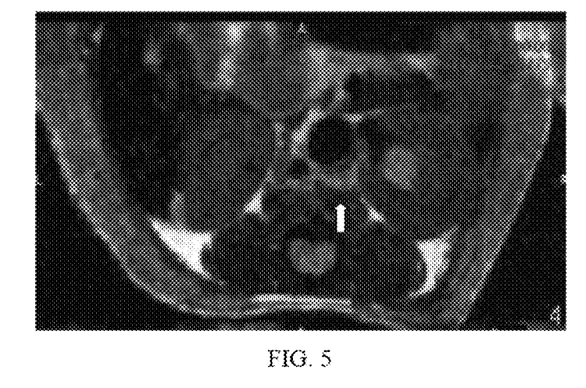
Figure 6:
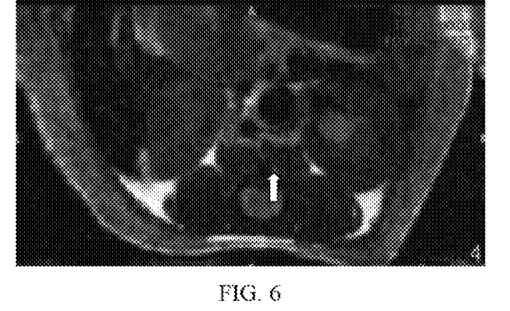
Figure 7:
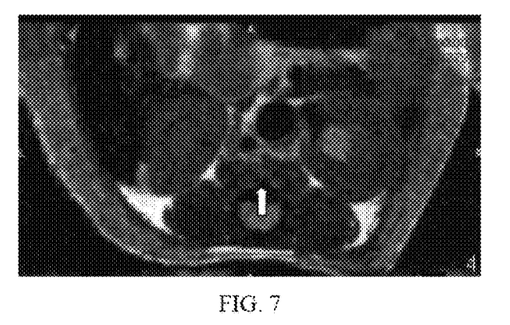
Figure 8:
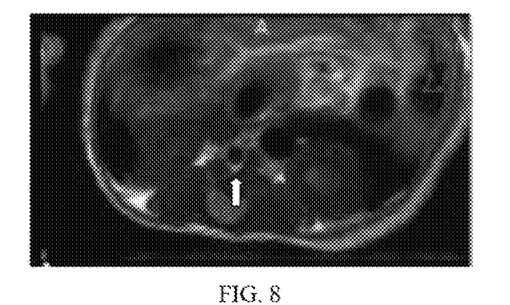
Figure 9:
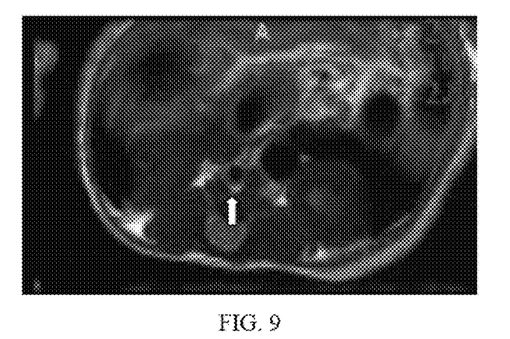
Figure 10:
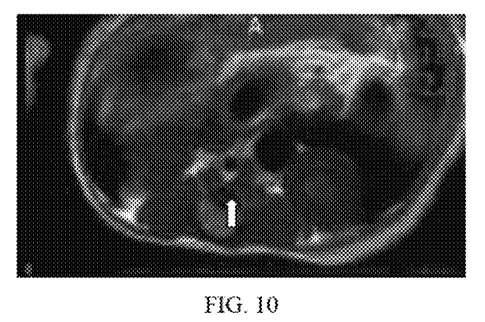
Figure 11:
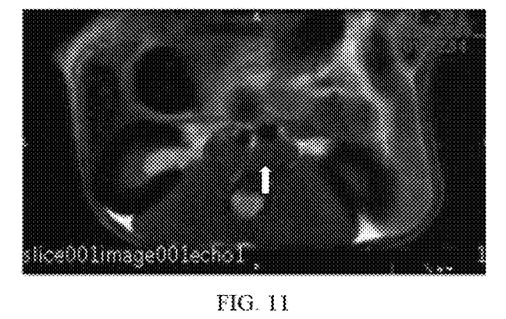
Figure 12:
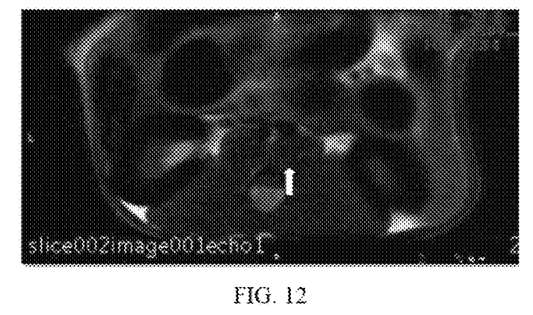
Figure 13:
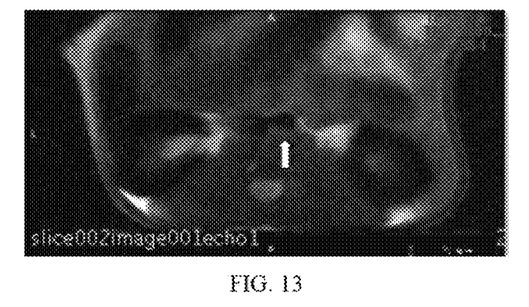
Figure 14:
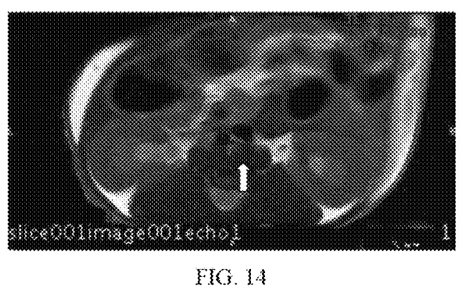
Figure 15:
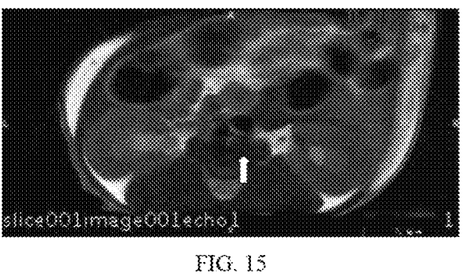
Figure 16:
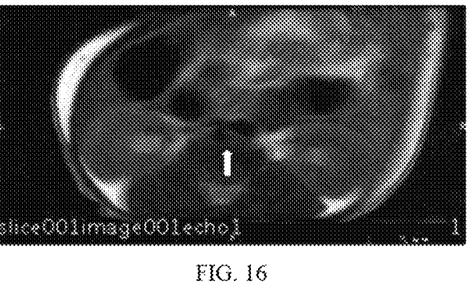
Figure 17:
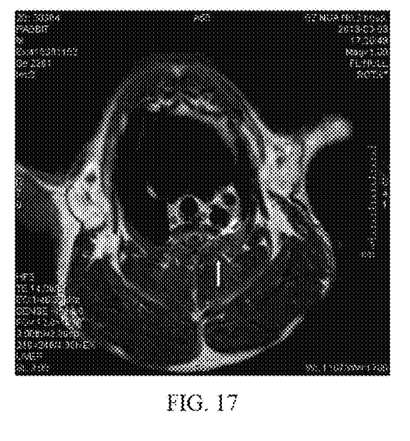
Figure 18:
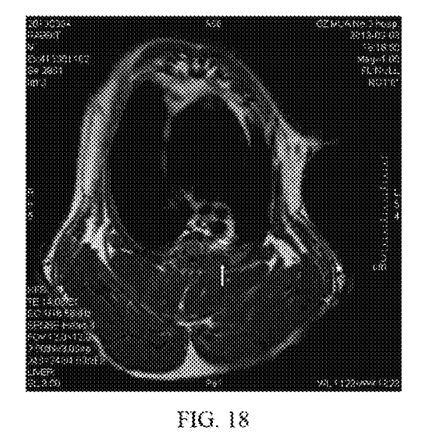
Figure 19:
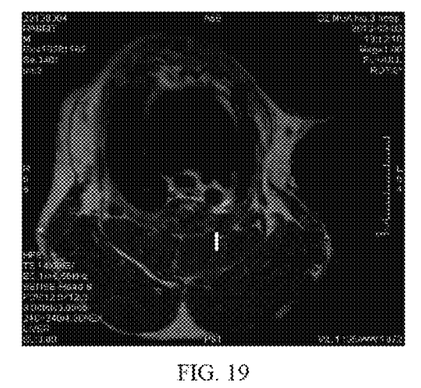
Figure 20:
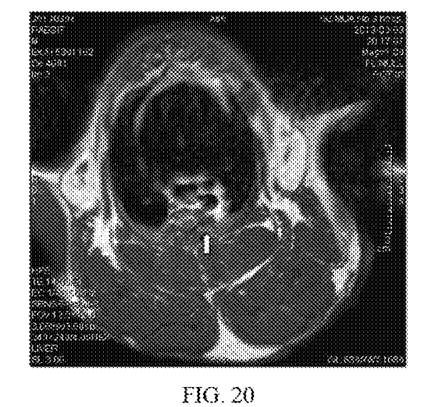
Figure 21:
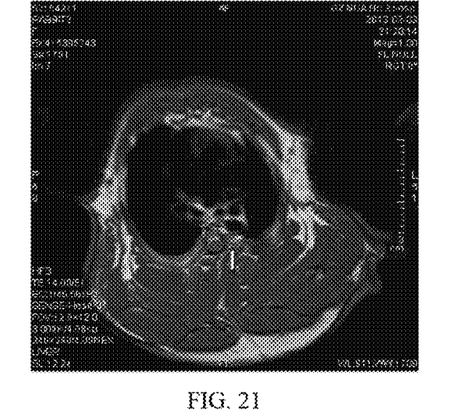
Figure 22:
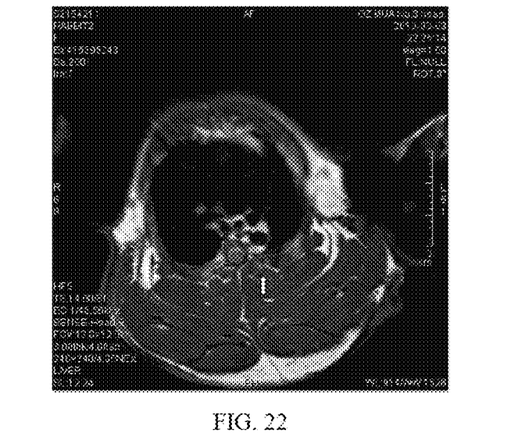
Figure 23:
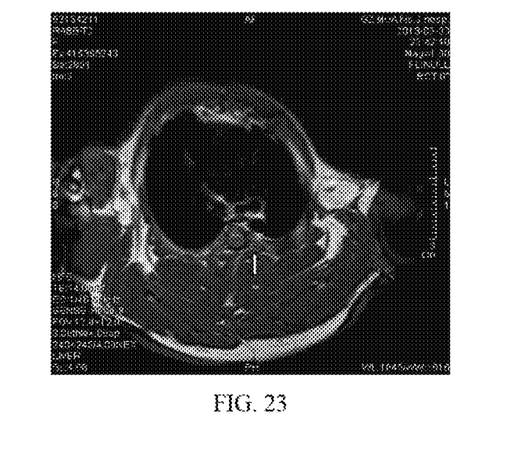
Figure 24:
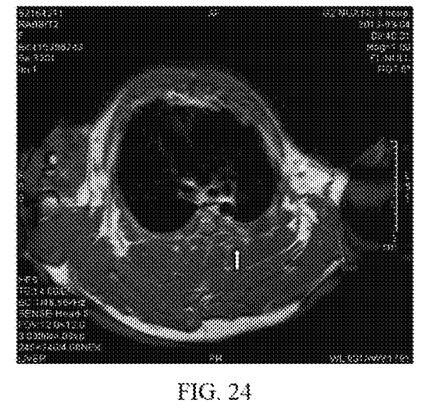
Figure 25:
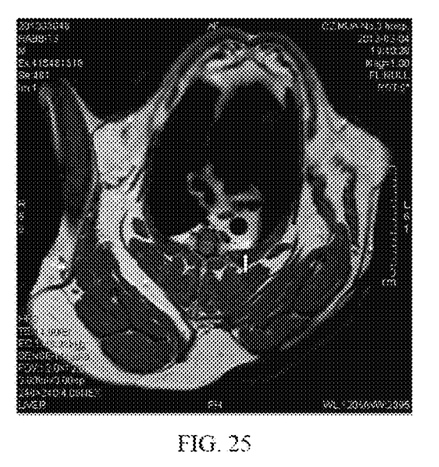
Figure 26:
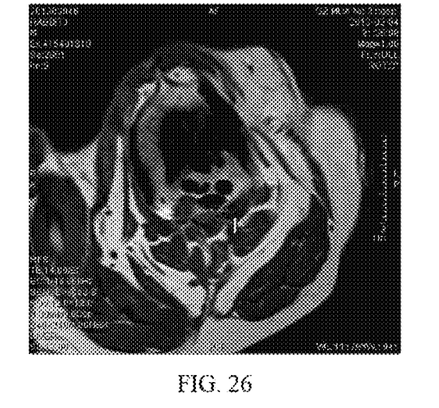
Figure 27:
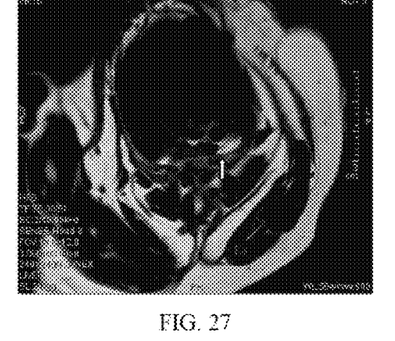
Figure 28:
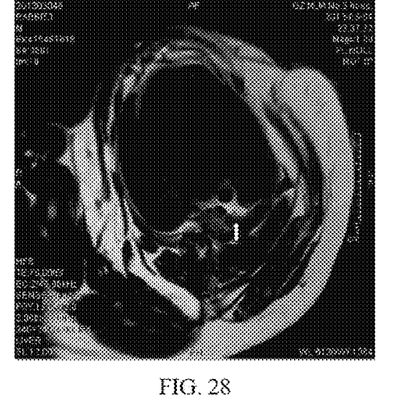
Figure 29:
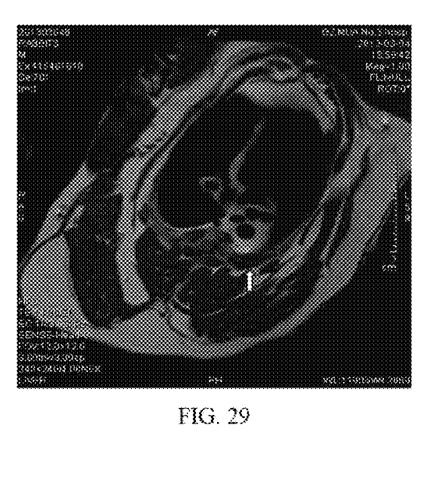
Figure 30:
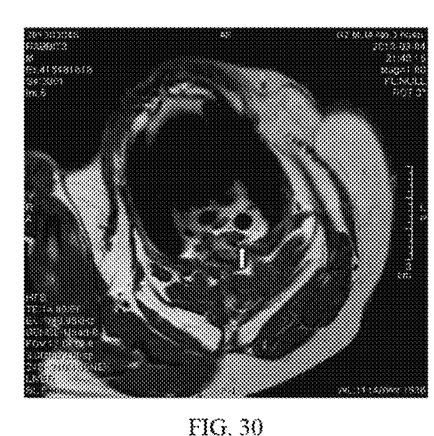
Figure 31:
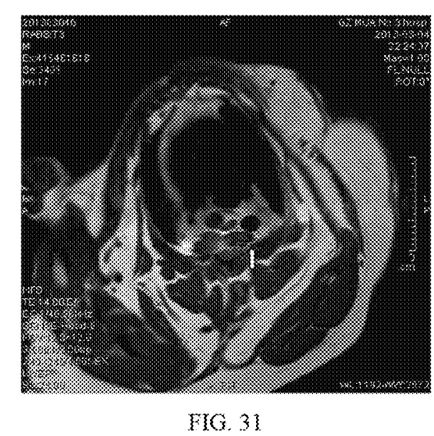
Figure 32:
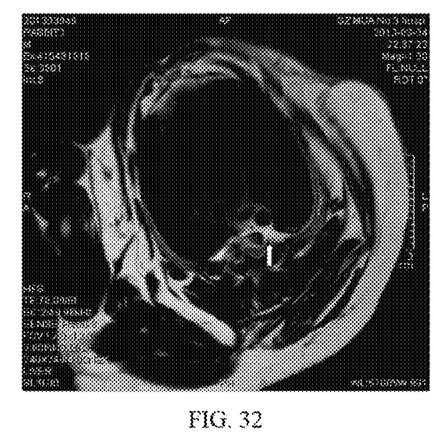

1. Detection of Biological and Physical Properties of MRI Targeting Nano-contrast Agent for Atherosclerosis Polyacrylamide gel electrophoresis analysis of the contrast agent of the present invention: in FIG. 1, 1: 100 bp Mark; 2: 5'-$NH_2$-targeting aptamer; 3-6: the final products of 0.1, 0.2, 0.5, 1 mL 3-aminopropyltriethoxysilane coated $Fe_3O_4$ coupling with 33 µg 5'-$NH_2$-targeting aptamer; 7: 3-aminopropyltriethoxysilane coated $Fe_3O_4$; the results of FIG. 1 show that the slime coated ferriferrous oxide nanoparticle vector in the contrast agent of the present invention can effectively connect to the targeting aptamer for atherosclerosis.

2. Detection of Magnetic Properties

The contrast agent of the present invention is detected by a vibration sample magnetometer and magnetic resonance, the detection result show that the saturated magnetization intensity of the vector is 108 emu·$g^{-1}$ Fe, the relaxation rate is $0.2842 \times 10^6$ $mol^{-1} \cdot s^{-1}$. The magnetization curve is a single curve passing through the origin point, indicating that the contrast agent of the present invention has superparamagnetism.

3. Magnetic Resonance Living Imaging of MRI Targeting Nano-contrast Agent for Atherosclerosis Respectively injecting the targeting nano-contrast agent for atherosclerosis and magnetic ferriferrous oxide nanoparticles to AS mouse soup and normal mouse group for magnetic resonance imaging in vivo, the results are in FIGS. 5-16. The results of FIGS. 5-16 show that in AS mouse group, at 30 minutes after injecting the targeting nano-contrast agent for atherosclerosis, the signal strength of AS lesion area shows decreasing trend, the vascular walls are not smooth, showing multiple spot signal defects at 45 minutes, the signal strength decreases to the lowest, after that the signal begin to enhance, until after 2 hours, the signal strength recovers to almost the same as that before the injection. In the normal animal group, after injecting the targeting nano-contrast agent for atherosclerosis, the signal strength of blood vessel walls has no significant change all the time.

Respectively injecting the targeting nano-contrast agent for atherosclerosis and magnetic ferriferrous oxide nanoparticles to AS New Zealand rabbit group and normal New Zealand rabbit group for magnetic resonance imaging in no the results are in FIGS. 17-32. FIGS. 17-32 show that in AS New Zealand rabbit group, at 1 hour after injecting the target nano-contrast agent for atherosclerosis, the signal strength of AS lesion area shows decreasing trend, the vascular walls are not smooth, showing spotted signal defects, at 2 hours, the signal strength decreases to the lowest, after that the signal begin to enhance, until after 3 hours, the signal strength recovers to almost the same as that before the injection. In the normal New Zealand rabbit group, the signal strength of blood vessel walls has no significant change all the time.

Above-mentioned embodiments only are preferred embodiments of the present invention, they cannot limit the scope of protection of the present invention, furthermore, all the non-substantial modifications and substitutions made by a person skilled in the art based on the present invention belong the scope of protection of the present invention.

What is claimed is:

1. A MRI targeting nano-contrast agent for atherosclerosis, comprising: a targeting aptamer for atherosclerosis and a vector connected to the targeting aptamer for atherosclerosis, wherein the targeting aptamer for atherosclerosis is a targeting aptamer fragment for atherosclerosis obtained through screening of macrophage-derived foam cells together with reverse screening of smooth muscle cells, endothelial cells, and THP-1 cells using a SELEX method; wherein the targeting aptamer is SEQ ID No: 1 or SEQ ID No: 2.

2. The MRI targeting nano-contrast agent for atherosclerosis according to claim 1, wherein the vector is a silane coated ferriferrous oxide nanoparticle vector; the targeting aptamer for atherosclerosis is covalently connected to a silane in the vector via glutaral as a bridge.

3. The MRI targeting nano-contrast agent for atherosclerosis according to claim 1, wherein a mass ratio of the vector and the targeting aptamer for atherosclerosis is (5-10):1.

4. The MRI targeting nano-contrast agent for atherosclerosis according to claim 2, wherein a ratio of a total mass of a plurality of ferriferrous oxide nanoparticles to a mass of the silane is 1:(3-8) in the vector.

5. The MRI targeting nano-contrast agent for atherosclerosis according to claim 4, wherein a mean particle size of the plurality of ferriferrous oxide nanoparticles is 10-15 nanometer and a total particle size of the silane coated ferriferrous oxide nanoparticle vector is 30-100 nanometer.

6. The MRI targeting nano-contrast agent for atherosclerosis according to claim 2, wherein a plurality of magnetic parameters thereof are: a $T_2$ relaxation rate of $0.2842 \times 10^6$ $mol^{-1} \cdot s^{-1}$, and a mass saturated magnetization intensity of 108 $emu \cdot g^{-1}$ Fe.

7. The MRI targeting nano-contrast agent for atherosclerosis according to claim 2, wherein the silane is a 3-aminopropylethoxysilane.

8. A method for preparing a MRI targeting nano-contrast agent for atherosclerosis,
wherein the MRI targeting nano-contrast agent for atherosclerosis comprises a targeting aptamer for atherosclerosis and a vector connected to the targeting aptamer for atherosclerosis, wherein the targeting aptamer for atherosclerosis is a targeting aptamer fragment for atherosclerosis obtained through screening of macrophage-derived foam cells together with reverse screening of smooth muscle cells, endothelial cells, and THP-1 cells using a SELEX method; wherein the targeting aptamer is SEQ ID No: 1 or SEQ ID No: 2;
wherein the vector is a silane coated ferriferrous oxide nanoparticle vector; the targeting aptamer for atherosclerosis is covalently connected to the silane in the vector via glutaral as a bridge;
wherein the method comprises the following steps:
1) preparing the silane coated ferriferrous oxide nanoparticle vector: using ferric chloride and ferrous sulfate as raw materials, refluxing the ferric chloride and ferrous sulfate under a nitrogen atmosphere, after refluxing, separating out ferriferrous oxide using a magnet, and refluxing the ferriferrous oxide with silane, after the reaction, obtaining a silane coated ferriferrous oxide nanoparticle vector by a separation using the magnet;
2) synthesizing of a contrast agent: washing the silane coated ferriferrous oxide nanoparticle vector obtained in step 1) with water and an alcohol alternately, dissolving a targeting aptamer and the silane coated ferriferrous oxide nanoparticle vector in at least one PBS solutions respectively, then adding the PBS solution of the targeting aptamer for atherosclerosis into the PBS solution of the silane coated ferriferrous oxide nanoparticle vector, and adding a glutaral, placing on a shaking table for vibration; separating a product with a magnet, removing the supernatant, and washing with the PBS solution.

9. The method for preparing the MRI targeting nano-contrast agent for atherosclerosis according to claim 8, wherein the step 1) is carried out according to the flowing steps:
a) preparing ferriferrous oxide: mixing ferric trichloride and ferrous sulfate at a molar ratio of (1.5-2.5):1, the temperature is set at 27-35° C. when refluxing, slowly dropwise adding ammonia water during the refluxing to pH>9, after curing for 20-40 minutes, raising the temperature to 60° C., continuously refluxing for 0.5-1.5 hours, then separating out ferriferrous oxide with the magnet, and washing with deionized water and anhydrous ethanol for 2-4 times respectively, to obtain ferriferrous oxide;
b) preliminary treating of the silane, adding the silane into deionized water and stirring, and dropwise adding glacial acetic acid, adjusting pH to 4-6;
c) coating: adding anhydrous ethanol to the ferriferrous oxide, then adding the silane solution, condensation and reflux, stirring for 3-6 hours at 55-65° C., stopping the heating, further stirring down to room temperature, taking the reaction liquid, separating using a magnet, removing the supernatant, washing with deionized water and then anhydrous ethanol for 2-4 times respectively.

10. The method for preparing the MRI targeting nano-contrast agent for atherosclerosis according to claim 8, wherein in the step 2), the pH of the employed PBS solution is 7.4.

11. The method for preparing the MRI targeting nano-contrast agent for atherosclerosis according to claim 10, wherein in the step 2), a rotating speed of the shaking table is 100 r/min, the temperature is 25° C., and a vibration time is 0.5-1.5 hours.

\* \* \* \* \*